US008470245B2

(12) United States Patent
Friedlaender et al.

(10) Patent No.: US 8,470,245 B2
(45) Date of Patent: Jun. 25, 2013

(54) PLASTIC REPROCESSING WITH CONTROLLED DECONTAMINATION

(75) Inventors: Thomas Friedlaender, Regensburg (DE); Maren Hofferbert, Regensburg (DE); Hans-Jurgen Straubinger, Pentling (DE)

(73) Assignee: Krones AG, Neutraubling (DE)

( * ) Notice: Subject to any disclaimer, the term of this patent is extended or adjusted under 35 U.S.C. 154(b) by 0 days.

(21) Appl. No.: 13/599,604

(22) Filed: Aug. 30, 2012

(65) Prior Publication Data

US 2013/0022504 A1    Jan. 24, 2013

Related U.S. Application Data

(62) Division of application No. 10/575,368, filed as application No. PCT/EP2004/011230 on Oct. 8, 2004, now Pat. No. 8,304,457.

(30) Foreign Application Priority Data

Oct. 13, 2003   (DE) .................................. 103 48 145

(51) Int. Cl.
*G01N 21/00*     (2006.01)

(52) U.S. Cl.
USPC .............. 422/67; 422/62; 422/68.1; 422/105; 422/119; 521/40; 436/43; 436/50; 436/55; 209/3.1; 209/3.2; 209/11; 209/12.1

(58) Field of Classification Search
USPC ............... 422/62, 67, 68.1, 105, 119; 436/43, 436/50, 55; 209/3.1, 3.2, 11, 12.1; 521/40; 134/18, 56 R See application file for complete search history.

(56) References Cited

U.S. PATENT DOCUMENTS

| 4,591,629 | A | | 5/1986 | E-Ghatta et al. |
| 4,921,936 | A | * | 5/1990 | Adams ........................... 528/389 |
| 5,049,647 | A | | 9/1991 | Al-Ghatta |
| 5,688,693 | A | | 11/1997 | Fine et al. |
| 5,899,392 | A | | 5/1999 | Hayward et al. |
| 6,103,774 | A | | 8/2000 | Rule |
| 6,509,537 | B1 | | 1/2003 | Krieg et al. |
| 6,533,124 | B1 | | 3/2003 | Tacito et al. |
| 2007/0068553 | A1 | | 3/2007 | Friedlaender et al. |

FOREIGN PATENT DOCUMENTS

| DE | 1002682 | 8/2001 |
| DE | 10348145 | 5/2005 |
| WO | WO-01/83112 A1 | 11/2001 |

* cited by examiner

*Primary Examiner* — Frances Tischler
(74) *Attorney, Agent, or Firm* — Marshall, Gerstein & Borun LLP

(57) ABSTRACT

A device for reprocessing used plastic containers including a system for analyzing the degree of contamination of the plastic, a system for determining decontamination process parameters as a function of the degree of contamination thus detected, and a system for controlled decontamination of the plastic according to the decontamination process parameters thus determined. The system for determining decontamination process parameters provides determined decontamination process parameters to corresponding decontamination control elements that are automatically adjusted depending on the degree of contamination.

7 Claims, 4 Drawing Sheets

PLASTIC REPROCESSING WITH CONTROLLED DECONTAMINATION

CROSS-REFERENCE TO RELATED APPLICATION

This application is a divisional of U.S. patent application Ser. No. 10/575,368 filed Sep. 21 2006, now issued as U.S. Pat. No. 8,304,457, which is the U.S. national stage under 35 U.S.C. §371 of international application no. PCT/EP2004/011230, having an international filing date of Oct. 8, 2004, the US national phase filing requirements having been perfected under 35 USC §371(c) on Sep. 21, 2006, and claims priority to German application no. 103 48 145.1 filed on Oct. 13, 2003.

FIELD OF THE DISCLOSURE

The disclosure relates to a method and a device for reprocessing used plastic containers, especially PET bottles.

BACKGROUND OF THE DISCLOSURE

Methods and devices for reprocessing used plastic containers are known. In most cases the labels are released and removed as the first step. Then in a next step a mill is used to pulverize the containers to flakes. The resulting mixture is washed and cleaned to remove any remaining residues of glue. Then the flakes are separated according to different types of plastic, e.g. PET and polyethylene.

Next, the flakes are cleaned in a decontamination step so that they can be reused to produce new plastic containers.

Thus for example, a decontamination process in which PET flakes from pulverized beverage bottles are subjected to a washing treatment in a washer is known from DE-10002682. Furthermore U.S. Pat. No. 5,688,693 describes a method in which highly contaminated bottles or flakes are identified and removed from the reprocessing operation.

However, the known processes are based on the problem that the decontamination process step of the reprocessing operation is adjusted to worst case conditions which means that the cleaning process is always performed, regardless of the degree of soiling of the starting material, in such a way that even the most contaminated plastic bottles and/or plastic flakes are adequately cleaned. Therefore, these known methods are not economical, even when an adequate cleaning is achieved.

SUMMARY OF THE DISCLOSURE

The object of the present disclosure is thus to provide a method and a device which will increase the profitability of reprocessing of used plastic containers, especially PET bottles, and will allow the required decontamination process step to be carried out under improved conditions.

According to this disclosure, the thod thus includes the following steps: a) analyzing the degree of contamination of the plastic, b) determining decontamination process parameters as a tinction of the degree of contamination found in step a), and c) controlled decontamination of the plastic according to the decontamination process parameters thus determined.

With this method, the decontamination step is automatically adapted to the actual contamination of the plastic, thanks to the determination of degree of contamination. By controlled decontamination, excess cleaning is thus prevented, and this yields a reprocessing operation that can be carried out more economically.

In a preferred embodiment, impurities present in the plastic and the respective concentration thereof can be ascertained in step a) of a preferred embodiment. With a contamination profile broken down in this way, it is possible to ascertain how the plastic is contaminated and how great the respective contamination is. Contaminants, i.e., impurities, are understood to refer to both substances that are hazardous to health and flavorings that would have harmful effects on the subsequent use of the recycled plastic containers when present even in small quantities due to their low perception threshold.

The contaminants detected may advantageously be combined into contaminant groups. The contaminants thus detected and the concentrations thereof are used in step b) to determine the decontamination process parameters. A determination as a function of all the contaminants detected may be very time-consuming and would thus lead to complicated control algorithms. It is therefore advantageous to combine individual components having similar properties. For example, hydrocarbons or several hydrocarbon subgroups having certain molecular weight ranges that are determined in advance could be combined here. It would also be conceivable to group the impurities according to physical properties, e.g., according to their diffusion constants.

In a preferred embodiment, a process temperature adapted to the degree of contamination may be determined as a decontamination process parameter in step b). Since the contaminants are usually not only at the surface of the plastic material but also in interior of the material, they must first diffuse to the surface, from which they can then he removed by washing, for example. According to the laws of diffusion, diffusion coefficients are a function of temperature, so it is possible to accelerate the decontamination process by adjusting the temperature for the prevailing level of contamination. For example, a higher process temperature will be selected for highly contaminated plastics than for less contaminated plastics.

In an especially advantageous embodiment of the method, a process duration adapted to the degree of contamination may be determined as a decontamination process parameter in step b). According to the diffusion law, the pulp flow density is a function not only of temperature but also of time, so the decontamination step may thus also be optimized by adjusting the retention time. For example, at a uniform process temperature, less contaminated plastic can be decontaminated more rapidly than highly contaminated plastic which should remain in the decontamination process for a longer period of time. Thus, a decontamination level which is sufficient to comply with food standards can be achieved at the end of the decontamination process for both degrees of contamination.

The degree of contamination of the plastic can conceivably be determined in step b) by adding up the concentrations of the contaminants or contaminant groups thus detected. The decontamination process parameters can be determined easily and thus quickly by such an estimation of the total contamination, with the decontamination being continued as a function of a degree of contamination that has been determined.

A weighting factor may expediently be assigned to the individual contaminants or contaminant groups as a function of an intensity of contamination that corresponds to the contaminant or contaminant group and then the degree of contamination is determined from the weighted summation of the contaminations of the contaminants and contaminant groups thereby detected. Through such a weighted summation, it is possible to take into account the fact that different contaminants cause different degrees of contamination. For example, in the case of flavorings, the perception threshold is relatively low, especially for lemons. Due to a high weighting factor for lemons, it is possible to take into account this substance in the determination of the decontamination process parameters in comparison with other substances.

In another embodiment, the decontamination parameters may be determined in step b) as a function of the concentrations of a predetermined number of contaminants or contaminant groups. Thus, for example, the optimized decontamination process parameters can be determined only on the basis of the ten contaminants occurring most commonly or only on the basis of the total hydrocarbons. For example, if the reprocessed plastic is not to be reused in the food industry, then contamination due to flavorings will play only a subordinate role and thus need not be taken into account in the determination of decontamination parameters. This makes is possible to adapt the process even better o the requirements of the material to be reprocessed.

In one variant of the invention, the decontamination process parameters can be determined independently of one another in step b) for at least two, especially for all the contaminants detected or contaminant groups detected, and in step c) the decontamination process parameters for which the profile of requirements is most stringent are used. Under the assumption that the decontamination takes place for the individual contaminants independently of one another, it is thus possible to assure in a simple manner that the decontamination process parameters selected for a given contamination profile are those for which adequate decontamination can be ensured with respect to all the contaminants detected.

In an especially advantageous embodiment, the decontamination parameters can be determined as a function of controllable threshold values in step b). Thus, depending on the desired type of recycling, the decontamination process can be adjusted in such a way that it is possible to ensure with sufficient accuracy that the purity required for that type of recycling is maintained.

Step c) can preferably be performed only when the degree of contamination exceeds a predetermined first threshold value. If the analysis shows that the degree of contamination of the plastic is so low that the reprocessing operation could be continued even without decontamination, then it is possible, thanks to such a predetermined threshold value, to skip this specific decontamination step, which would further accelerate the process and thus make it more economical.

Preferably, the plastic can be re-shredded between process steps b) and c) if it is found that the degree of contamination exceeds a predetermined second threshold value. Re-shredding reduces the length of the diffusion path and thus also reduces the time required to bring the contaminants to the surface of the plastic. Therefore, the desired degree of purity can be achieved in a shorter period of time, by comparison, in a case of severe contamination in which adequate success would otherwise be achieved only by an excessively long decontamination time. The second threshold value is preferably higher than the first threshold value.

In a preferred embodiment, if the degree of contamination exceeds a predetermined third threshold value, then the plastic can be sorted out and removed from the reprocessing operation instead of going through steps b) and c). This third threshold value is selected so that any plastic having a contamination level so high that decontamination is no longer economically feasible will be removed from the process and not recycled. This further contributes to the economic feasibility of the process. The third threshold value here is advantageously higher than the first and third threshold values.

The decontamination process parameters can advantageously be determined in step b) with the help of a numerical diffusion model, where the degree of contamination is a parameter of the model. With the laws of diffusion and the known diffusion coefficients of the contaminants and/or contaminant groups, the optimized temperature and/or duration of the decontamination process can be determined again continuously on the basis of the measured degree of contamination.

Fortunately in step b), the decontamination process parameters can also be determined by comparing the degree of contamination with a predetermined data record. Such a data record can be compiled either experimentally or through model calculations. Depending on the concentrations and/or the presence of contaminants, it is thus possible to determine the parameters that fit the respective situation by adjusting the measured values with values saved in a database.

In an especially preferred embodiment, the plastic may be added to one of at least two partial quantities, depending on the degree of contamination thus determined, between steps a) and b), and in step b) decontamination process parameters are determined for each of the at least two partial quantities and in step c) decontamination is performed according to the decontamination process parameters thus determined for each of the partial quantities. This permits greater flexibility in the process because, for example, plastics with a similar degree of contamination are collected in different partial quantities and then the partial quantities are decontaminated independently of one another. It is also possible to set up buffer storage where the partial quantities can be stored until enough material has been collected, only then continuing with the decontamination. This makes it possible to utilize the process more economically.

According to this disclosure, the device for carrying out the method includes a system for analyzing the degree of contamination of the plastic, a system for determining decontamination process parameters as a function of the degree of contamination thus detected and a system for controlled decontamination of the plastic according to the decontamination process parameters thus determined.

With this device, the decontamination can be automatically adjusted to the actual contamination of the plastic thanks to the determination of the degree of contamination. Excessive cleaning is thus prevented by the controlled decontamination.

The system for performing the analysis may advantageously include a mass spectrometer. A mass spectrometer makes it possible to determine the contaminants according to type and quantity and are therefore especially suitable for the device according to this disclosure.

The mass spectrometer is advantageously configured so that it essentially determines the degree of contamination in real time. By means of a rapid analysis of the degree of contamination of all flakes in conjunction with a rapid determination of the decontamination process parameters, it is thus possible to accelerate the entire process.

BRIEF DESCRIPTION OF THE DRAWINGS

Exemplary embodiments of the present disclosure are depicted in the drawings and explained in greater detail below; the drawings show.

DETAILED DESCRIPTION OF THE DISCLOSURE

Figure 1:
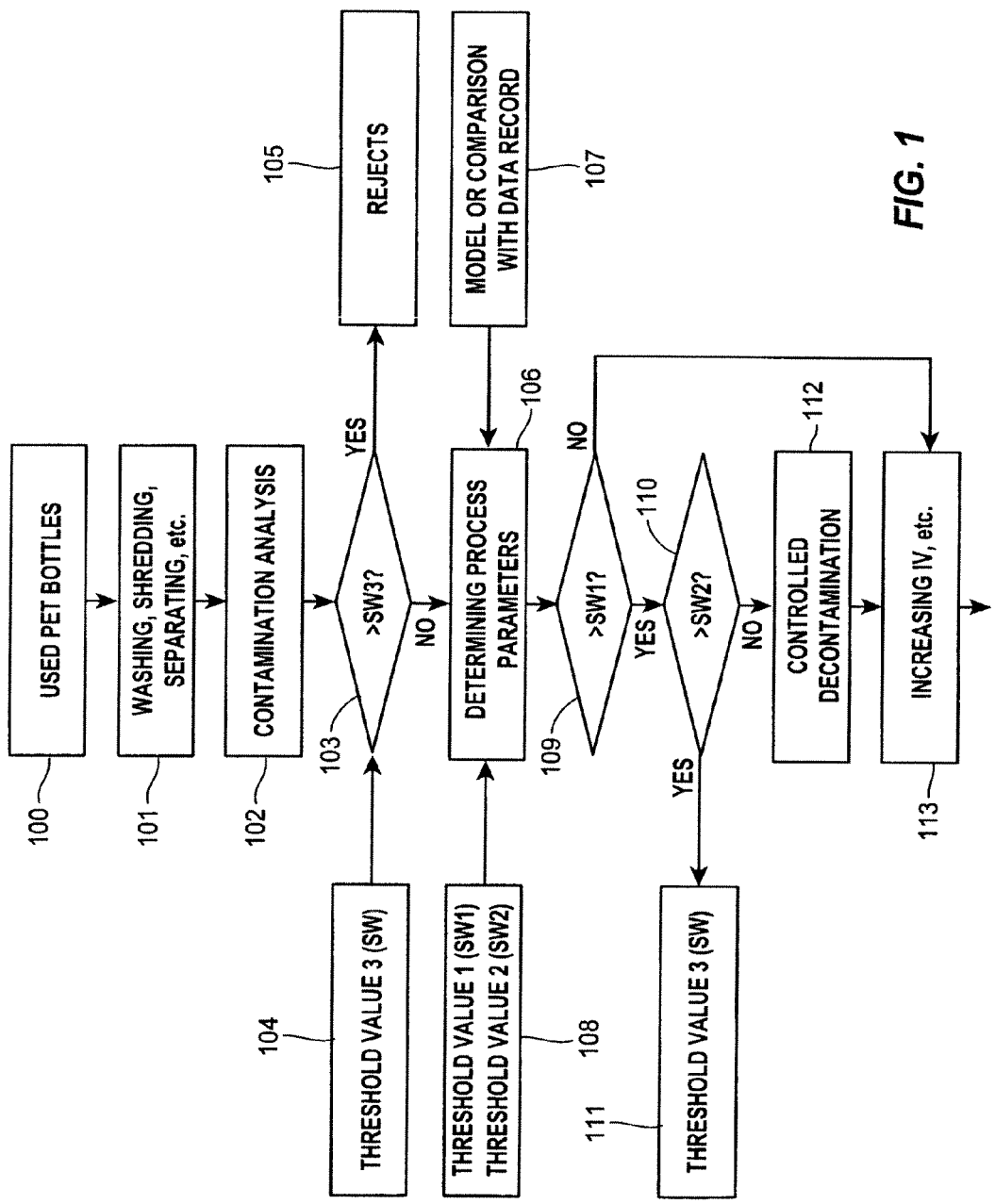
FIG. 1 a flow chart of a first exemplary embodiment of the disclosed process.

FIG. 1 shows a flow chart of a first embodiment of the inventive method for reprocessing used plastic containers, especially PET bottles. In step 100, used PET bottles are supplied. They are washed and shredded in several steps 101 thereafter. Furthermore, the various materials, e.g., PET, polyethylene of the caps, paper or plastic labels, metal caps and adhesives are separated. The process steps described below pertain only to the PET flakes formed by shredding.

In step 102 the degree of contamination of all plastic flakes is analyzed according to process step a). To do so, for example, a mass spectrometer is used, creating a contamination profile based on the contaminant and amount of contamination. From the contamination profile thereby determined, the degree of contamination is then determined. The degree of contamination can be determined in various ways. For example, the contamination level is determined by adding up the concentrations of the contaminants detected. In a second variant, a weighted sum may be calculated by assigning a weighting factor to a contaminant depending on the intensity of contamination with this contaminant, then multiplying this weighting factor times the respective concentration and only then performing the total addition. This makes it possible to ensure that low concentrations of highly contaminated substances will play a greater role in determining the degree of contamination. According to another variant, several contaminants having similar properties such as hydrocarbons or flavoring agents are combined into groups and a degree of contamination is determined for each component of this group according to the methods already described.

In step 103, this degree of contamination that was analyzed in step 101 is compared with a predetermined threshold value 3 (SW 3) which is made available in step 104. This threshold value 3 may be either fixedly predetermined or adjusted by the operator of a reprocessing plant in accordance with circumstances. If the degree of contamination thus determined is above this threshold value 3, then the corresponding plastic flakes are sorted out and removed from the process because they are too highly contaminated. For the case when several degrees of contamination have been determined, there is the option of sorting out the plastic flakes only if all degrees of contamination are above the particular threshold values 3 or the plastic flakes are sorted out when there is at least a degree of contamination above the respective threshold value 3. This makes it possible, for example, for PET bottles to be sorted out even if they have not been contaminated by hydrocarbons but instead only traces of flavorings have been found in them.

If the degree of contamination is below threshold value 3, then in step 106 the decontamination process parameters corresponding to the degree of contamination found in step 102 are determined according to process step b). To determine these parameters, either a numerical model based on the laws of diffusion is used or the degrees of contamination are compared with a predetermined data record in step 107. If the numerical method is used, then the required duration of the decontamination step can be calculated on the basis of the concentrations thus determined at a predetermined decontamination process temperature. Conversely in the case of a fixedly predetermined decontamination time, the process temperature that would be required to adequately clean the plastic flakes during this predetermined process time can be calculated. If the calculation reveals a temperature above a critical transition temperature of 220° C., for example, then the process time is lengthened accordingly. Instead of calculating the decontamination process parameters anew in each case, in one variant it is also possible to determine the decontamination process parameters by comparing the degrees of contamination with a predetermined data record (the latter being based on the same laws as the numerical model).

In determination of the process parameters in step 106, a threshold value 1 and a threshold value 2 which are made available in step 108 are also taken into account. The threshold value 1 indicates for which degree of contamination a decontamination is required at all subsequently. If the contamination is below this limit, the plastic can be processed further directly without a decontamination step. Threshold value 2 indicates beyond which degree of contamination it is advantageous to re-shred the plastic to shorten the diffusion paths to thereby accelerate the decontamination. These threshold values may be predetermined and/or adjusted by the user to thereby adapt the process so that the reprocessed material conforms to quality demands, which may vary according to the use of the reprocessed material.

Thus if the degree of contamination is below threshold value 1 (step 109) then the special decontamination step in the process is skipped and the reprocessing operation goes directly to performing the IV-increasing step (IV=intrinsic viscosity) which serves to impart once again to the PET flakes the properties required to be able to manufacture PET bottles from them again (step 113). A certain decontamination also takes place here because of the heating.

If the degree of contamination is above the threshold value 1, then a check is performed in the next step 110 to determine whether the degree of contamination is above the threshold value 2. If this is the case, then in step 111 the plastic flakes are re-shredded and only then sent to the decontamination step 112. If the degree of contamination is below the threshold value 2, then the method is continued directly with decontamination step 112.

Decontamination step 112 is performed with the process parameters determined in step 106 and thus represents a controlled process step according to process step c). The final control elements for the individual process parameters such as temperature, decontamination time, etc., are usually adjusted automatically. Then the plastic flakes are sent to the next process step 113, the IV-increasing step, as described above.

Other variants can also be implemented by starting with this first exemplary embodiment. For example, it is not absolutely necessary to shred the bottles before the contamination analysis and instead unshredded PET bottles can also be checked for their degree of contamination. In another variant, before the contamination analysis step 102, the PET flakes could be separated, separating PET flakes that originate from thicker bottle head parts from PET flakes from the remaining bottle. This is of interest because the PET flakes of the bottle head are thicker than those from the remainder of the bottle; it is more difficult to clean them because contaminants are situated deeper in the PET material. In the exemplary embodiment described here, the process temperature and process time are referred to as decontamination process parameters. However, these are only two examples of process parameters because the cleaning agent used for decontamination might also be adjustable.

Figure 2:
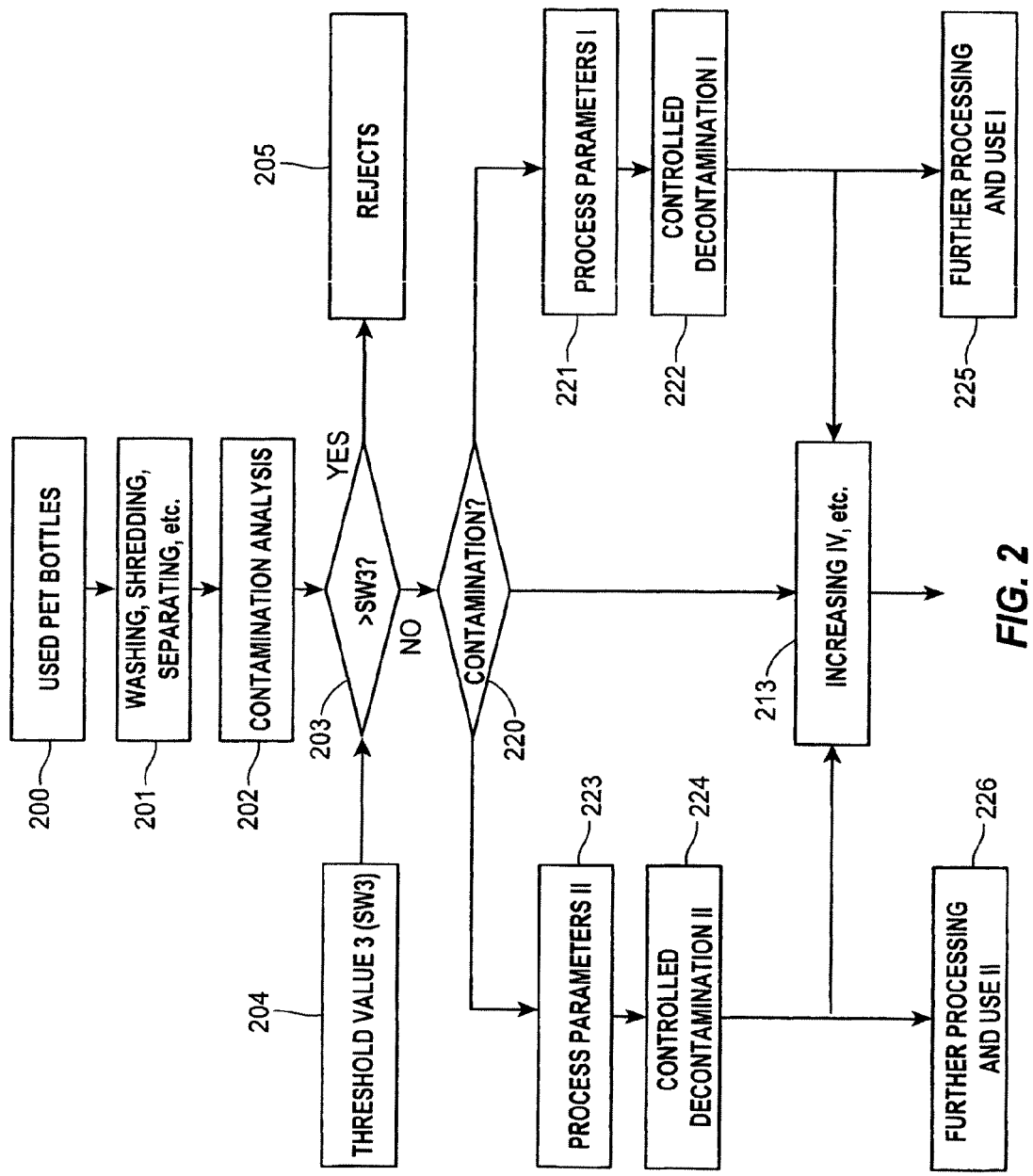
FIG. 2 a flow chart of a second embodiment of the disclosed process.

FIG. 2 shows a second embodiment of the method for reprocessing used plastic containers. In this figure, process steps 200 through 205 and 213 correspond to process steps 100 through 105 and 113 of the first exemplary embodiment illustrated in FIG. 1. Process steps 200 through 205 and 213 have the same features as the corresponding process steps in the first exemplary embodiment and therefore will not be described in detail below.

The essential difference with respect to the first embodiment is that after analyzing the contamination (process step a), several processes can be performed in parallel. For example, if it has been determined in step 203 that the allowed degree of contamination is below the maximum degree of contamination as defined by the threshold value 3, then a decision is made in step 220 regarding whether the degree of contamination is low, moderate or high. Low, moderate and high as used here each denote a range of contamination, but the limits between these ranges are predetermined or can be selected freely by the user.

If it has been found that the degree of contamination is low, then no decontamination is performed as in the first exemplary embodiment and the method proceeds with the next process step 213, increasing the intrinsic viscosity IV.

If a degree of contamination in the moderate contamination range has been found, then in process step 221 the fitting process parameters I are determined (process step b) and then the decontamination is performed in such a manner that it is controlled by the process parameters I thus determined (step 222, process step c). The process parameters were determined exactly as already described in conjunction with the first exemplary embodiment. As already described in the first exemplary embodiment, the final control elements for adjusting the decontamination process parameters are set automatically according to the process parameters thus determined. Then the process is continued with step 213, increasing the intrinsic viscosity IV.

If it has been found in step 220 that the degree of contamination is in the range of high contamination, then in process step 223, a second set of process parameters II is determined (process step b) and next the decontamination is performed in such a manner that it is controlled according to these second process parameters II (step 222, process step c). As already described in the first exemplary embodiment, the final control elements here are set automatically according to the process parameters thus determined for adjusting the decontamination process parameters. Then the process here again is continued with step 213.

In one variant the three partial quantities are processed further in different ways depending on their respective degrees of decontamination. For example, the limit values between the various contamination levels can be set at low, moderate or high, so that the process is carried out for the low and moderate partial quantities of decontamination in such a way that the PET flakes can then be reused for production of beverage bottles whereas the partial quantity having a high degree of contamination—which could not be decontaminated economically to such an extent that it would be acceptable for use in the food industry—is processed further (226) for use in a different application where demands are lower.

In another variant, it is conceivable for the steps 223, 224 and 221, 222 not to be performed in parallel but instead for a buffer storage to be set up, material with the same degree of contamination to be stored temporarily, and as soon as enough material is in the buffer storage, the respective suitable decontamination for it is performed. For example, first one or more batches may be sorted out and then decontaminated with the partial quantity for which decontamination is achieved most rapidly and then the process is continued with the more heavily contaminated partial quantity and/or one may wait until this partial quantity is large enough.

Figure 3:
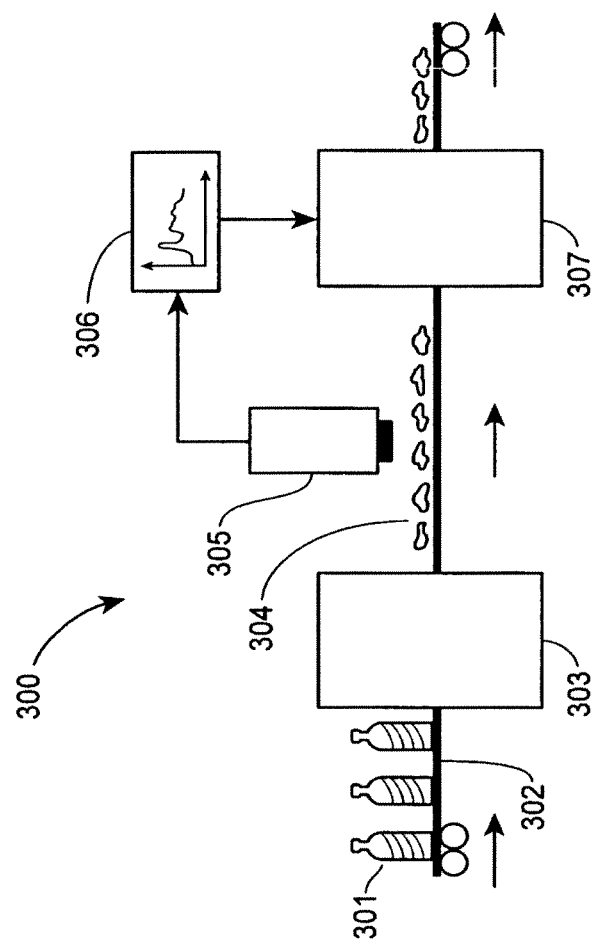
FIG. 3 a schematic view of a first embodiment of the disclosed process.

FIG. 3 shows an embodiment of a device for performing the inventive method for reprocessing used plastic containers, especially PET bottles. Used PET bottles 301 are charged to a conveyor belt 302. In a first section 303, the bottles 301 are washed and shredded. This does not show the zone in which the different materials are separated from one another. Then the prewashed PET flakes 304 emerge from section 303 and are analyzed by a contamination analysis device 305 such as a mass spectrometer, for example, in a continuous stream to determine their degree of contamination. The analytical device 305 forwards the data thus compiled with regard to the degree of contamination to the control unit 306 which determines the process parameters corresponding to the degree of contamination and automatically forwards them to the corresponding final control elements such as a temperature regulator, the process time setting, etc. in decontamination step 307 of device 300. The plastic flakes 304 enter this decontamination section 307 where they are cleaned in accordance with their degree of contamination, which can take place in a continuous stream or in batches. The PET flakes 304 then emerge from the decontamination section 307 and can then be treated further.

It is quite conceivable for the quality of decontamination to be tested after departure from the decontamination section, and if it is found that the decontamination has not been adequate, the process parameters may then be checked again and adjusted, if necessary, i.e., forming a closed control circuit with regard to the decontamination parameters.

Figure 4:
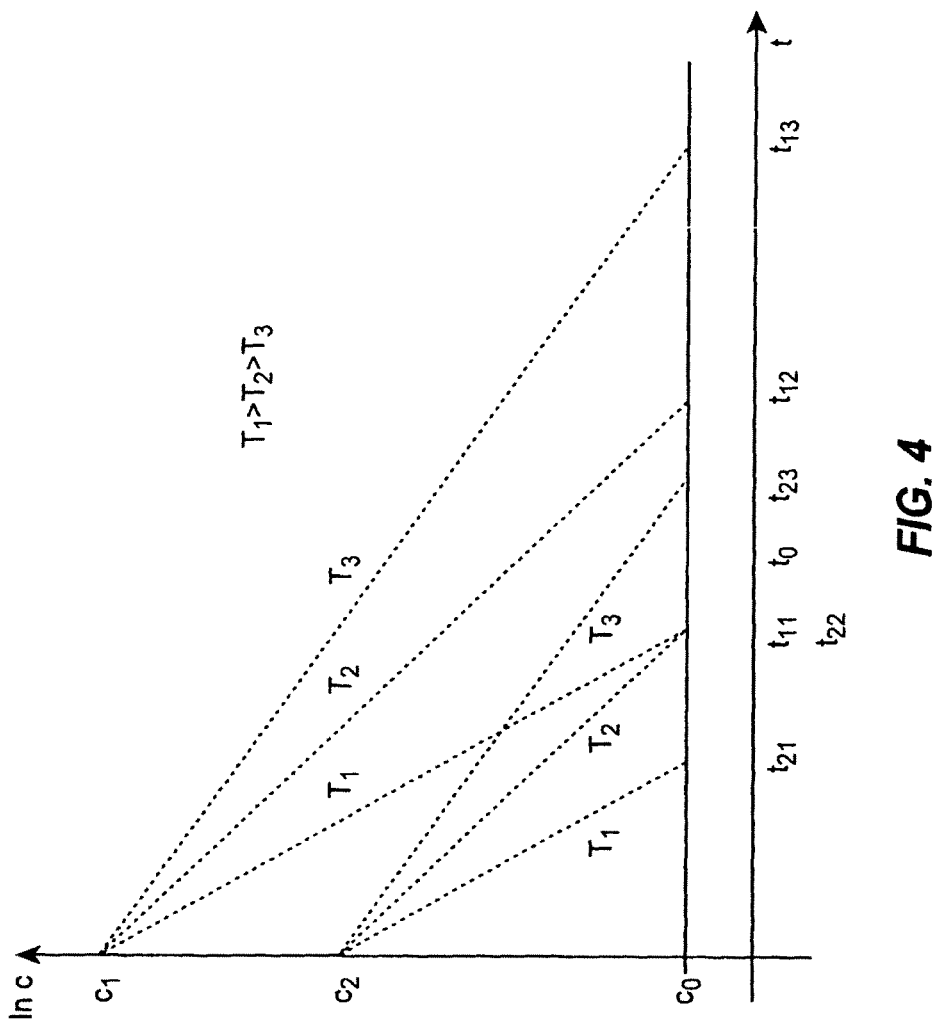
FIG. 4 an example of the possible adaptation of the decontamination process parameters as a function of a contamination level detected as well as the time and the temperature.

FIG. 4 shows an example of how the process parameters of temperature and time can be controlled on the basis of the detected concentration of a contaminant. The logarithm of the concentration of the contaminant is plotted on the Y axis and time is plotted on the X axis. According to the diffusion law, the logarithm of the concentration decreases linearly with time at a constant temperature. For example, if a concentration C1 is measured and is to be returned to a level C0, then a time t11 will be required to do so at the temperature T1. At the lower temperature T2, a time t12 would be needed to accomplish the same thing and at an even lower temperature T3 a time t13 would be needed. If the decontamination is to be performed in a time period of max, t0, then this can be achieved only at a process temperature T1 in the case of contamination with a concentration C1. However, if the detected concentration level is C2, it can be seen that the process temperature is T2 within the time t0. However, if the higher temperature T1 is retained, the desired level C0 is reached after a time of only t21.

It can thus be recognized on the basis of FIG. 4 that decontamination can be optimized by analyzing the degree of contamination and determining suitable decontamination process parameters. An upper limit of approximately 230° C. will usually be set for the process temperature.

The invention claimed is:

1. A device for reprocessing used plastic containers, comprising:
   a system for analyzing a degree of contamination of the plastic,
   a system for determining decontamination process parameters as a function of the degree of contamination thus detected,
      wherein a process temperature adapted to the degree of contamination is determined as a decontamination process parameter, and/or wherein a process time that is adapted to the degree of contamination is determined as a decontamination process parameter, and a system for controlled decontamination of the plastic according to the decontamination process parameters thus determined wherein the system for determining decontamination process parameters performs after the system for analyzing the degree of contamination of the plastic, and wherein the system for determining decontamination process parameters provides determined decontamination process parameters to corresponding decontamination control elements that are automatically adjusted depending on the degree of contamination.

2. The device according to claim 1, characterized in that the system for performing the analysis comprises a mass spectrometer.

3. The device according to claim 2, characterized in that the mass spectrometer is configured so that the degree of contamination is determined essentially in real time.

4. A device for reprocessing used plastic containers, comprising:
- a system for analyzing a degree of contamination of the plastic;
- a system for determining decontamination process parameters as a function of the degree of contamination thus detected;

wherein a process temperature adapted to the degree of contamination is determined as a decontamination process parameter, and/or wherein a process time that is adapted to the degree of contamination is determined as a decontamination process parameter; and a system for controlled decontamination of the plastic according to the decontamination process parameters thus determined, the system for controlled decontamination including one or more decontamination control elements that are automatically adjusted depending on the actual degree of contamination of the plastic.

5. The device of claim 4, wherein the system for determining decontamination process parameters performs after the system for analyzing the degree of contamination of the plastic.

6. The device of claim 4, wherein the one or more decontamination control elements includes one or more of a temperature regulator and a process time device.

7. The device of claim 4, wherein the one or more decontamination control elements receive determined decontamination process parameters from the system for determining decontamination process parameters.

* * * * *